United States Patent
Ernst et al.

(10) Patent No.: US 8,586,794 B2
(45) Date of Patent: Nov. 19, 2013

(54) 5-ISOPROPYL-3-AMINOMETHYL-2-METHYL-1-AMINO-CYCLOHEXANE (CARVONE DIAMINE), AND METHOD FOR THE PRODUCTION THEREOF

(75) Inventors: Martin Ernst, Heidelberg (DE); Alfred Oftring, Bad Duerkheim (DE); Kathrin Wissel-Stoll, Ludwigshafen (DE); Oemer Uensal, Mainz (DE); Stephan Freyer, Neustadt (DE); Ansgar Gereon Altenhoff, Heidelberg (DE); Wolfgang Staffel, Waldsee (DE)

(73) Assignee: BASF SE (DE)

( * ) Notice: Subject to any disclaimer, the term of this patent is extended or adjusted under 35 U.S.C. 154(b) by 157 days.

(21) Appl. No.: 13/055,604

(22) PCT Filed: Jul. 13, 2009

(86) PCT No.: PCT/EP2009/058888
§ 371 (c)(1),
(2), (4) Date: Jan. 24, 2011

(87) PCT Pub. No.: WO2010/009995
PCT Pub. Date: Jan. 28, 2010

(65) Prior Publication Data
US 2011/0124918 A1    May 26, 2011

(30) Foreign Application Priority Data
Jul. 25, 2008    (EP) .................................... 08161181

(51) Int. Cl.
| C07C 209/00 | (2006.01) |
| C07C 211/00 | (2006.01) |
| C08G 63/48 | (2006.01) |
| C08G 63/91 | (2006.01) |
| C08L 67/00 | (2006.01) |
| C08L 67/02 | (2006.01) |

(52) U.S. Cl.
USPC ........... 564/446; 564/449; 564/453; 564/462; 525/25

(58) Field of Classification Search
None
See application file for complete search history.

(56) References Cited

U.S. PATENT DOCUMENTS

| 5,371,292 A | 12/1994 | Merger et al. |
| 5,530,127 A | 6/1996 | Reif et al. |
| 5,536,691 A | 7/1996 | Breitscheidel et al. |
| 5,696,048 A | 12/1997 | Breitscheidel et al. |
| 6,022,988 A | 2/2000 | Fischer et al. |
| 2010/0036168 A1 | 2/2010 | Ernst et al. |

FOREIGN PATENT DOCUMENTS

| CA | 1239415 A | 7/1988 |
| DE | 19836474 A1 | 2/2000 |
| EP | 0128382 A1 | 12/1984 |
| EP | 0394058 A1 | 10/1990 |
| EP | 0449089 A1 | 10/1991 |
| EP | 0636409 A1 | 2/1995 |
| EP | 0696572 A1 | 2/1996 |
| EP | 0742045 A1 | 11/1996 |
| EP | 0895984 A1 | 2/1999 |
| EP | 0976723 A2 | 2/2000 |
| WO | WO-99/12880 A1 | 3/1999 |
| WO | WO-2004/060866 A2 | 7/2004 |
| WO | WO-2008/077852 A1 | 7/2008 |
| WO | WO-2010/009995 A2 | 1/2010 |

OTHER PUBLICATIONS

EFSA Journal (2009) 878, 1-28.*
Reitsema, "Nitrosochloride Syntheses and Preparation of Carvone," *Journal of Organic Chemistry* (1958), pp. 2038-2039.
Tanabe, et al., "Definition and Classification of Solid Acids and Bases," *Studies in Surface Science and Catalysis*, (1989), vol. 51, pp. 1-3.
Elliott, et al,, "2,4-Dimethylphenylacetic Acid from Cyanodihydrocarvone," *Chemistry and Industry*, (Jul. 8, 1967), vol. 2, p. 1175.

* cited by examiner

*Primary Examiner* — Clinton Brooks
(74) *Attorney, Agent, or Firm* — Novak Druce Connolly Bove + Quigg LLP

(57) ABSTRACT

The present invention relates to 5-isopropyl-3-aminomethyl-2-methyl-1-aminocyclohexane (carvonediamine) and to a process for preparation thereof by a) reacting carvone with hydrogen cyanide, b) then reacting the carvonenitrile obtained in stage a) with ammonia in the presence of an imine formation catalyst and c) then reacting the carvonenitrile imine-containing reaction mixture obtained in stage b) with hydrogen and ammonia over hydrogenation catalysts.
The present invention further relates to the use of carvonediamine as a hardener for epoxy resins, as an intermediate in the preparation of diisocyanates, as a starter in the preparation of polyetherols and/or as a monomer for polyamide preparation.

19 Claims, No Drawings

5-ISOPROPYL-3-AMINOMETHYL-2-METHYL-1-AMINO-CYCLOHEXANE (CARVONE DIAMINE), AND METHOD FOR THE PRODUCTION THEREOF

RELATED APPLICATIONS

This application is a national stage application (under 35 U.S.C. §371) of PCT/EP2009/058888, filed Jul. 13, 2009, which claims benefit of European Application No. EP 08161181.6, filed Jul. 25, 2008.

The present invention relates to 5-isopropyl-3-aminomethyl-2-methyl-1-aminocyclohexane (carvonediamine) and to a process for preparation thereof by a) reacting carvone with hydrogen cyanide, b) then reacting the carvonenitrile obtained in stage a) with ammonia in the presence of an imine formation catalyst and c) then reacting the carvonenitrile imine-containing reaction mixture obtained in stage b) with hydrogen and ammonia over hydrogenation catalysts.

The present invention further relates to the use of carvonediamine.

Cycloaliphatic diamines find use as hardeners for epoxy resins, as intermediates in the preparation of diisocyanates—which play an important role in the preparation of polyurethanes—, as starters in the preparation of polyetherols and as monomers for polyamide preparation.

The structure of the diamine used can influence the properties of the polymer materials prepared from the diamines, such as weathering stability, hydrolysis stability, chemical stability, light stability, and electrical and mechanical properties. However, it can also exert an influence on the processability and the processing of the diamines to the corresponding polymer materials—for example the hardening of epoxy resins.

Cycloaliphatic diamines used industrially are, for example, isophoronediamine (IPDA), bis(4-aminocyclohexyl)methane (PACM) and 1,2-diaminocyclohexane (DACH). PACM and DACH can be synthesized by hydrogenating the corresponding aromatic compounds, such as 4,4'-diaminodiphenylmethane or o-phenylenediamine. DACH is also obtained as a by-product in hexamethylenediamine production.

In DACH and PACM, both amino groups are substituted directly on the aliphatic ring and thus have the same or at least a similar reactivity.

For certain applications and properties, it may be advantageous when the two amino groups of the diamine have a different reactivity, since this influences the processing and hardening behavior. For example, in IPDA, an amino group resides directly on the aliphatic ring, while the other amino group is bonded to the aliphatic ring via a methylene bridge. IPDA is generally prepared by adding hydrogen cyanide onto isophorone to give isophoronenitrile and then hydrogenating in the presence of ammonia to give IPDA.

EP-A1-0394058 likewise discloses cycloaliphatic diamines with amino groups of different reactivity. Nitration of alkyl phenyl ketones affords nitrophenyl alkyl ketones, which are converted in the presence of hydrogen and ammonia to (aminophenyl)alkylamines. These are subsequently reduced to the corresponding (aminocyclohexyl)alkylamines. The yield in the last hydrogenation stage is about 80 to 90%.

EP-A1-0895984 describes the preparation of cycloaliphatic diamines with amino groups of different reactivity by reductive amination of alkyl-substituted 3-formylcycloalkanones. Alkyl-substituted 3-formylcycloalkanones are in turn obtainable by reacting alkyl-substituted cycloalkenones and formaldehyde. Proceeding from the cycloalkenones used, the yield of alkyl-substituted cycloaliphatic diamines is in the range of 50 to 60%.

IPDA is typically prepared from acetone, while the aforementioned alkyl-substituted cycloalkyldiamines are generally based on cyclohexene. Both acetone and cyclohexene are generally obtained from the petrochemical raw material naphtha.

It was an object of the present invention to provide a cycloaliphatic diamine which can also be prepared on the basis of renewable raw materials. Reverting to renewable raw materials can contribute to sustainment of exhaustible resources and enables sustainable economic activity.

It was a further object of the present invention to synthesize a cycloaliphatic diamine which, similarly to IPDA, has both an amino group bonded directly to the aliphatic ring and an amino group joined to the aliphatic ring via a methylene group. A diamine based on renewable raw materials which has a similar reactivity to IPDA and can be used as a substitute for IPDA in many cases should thus be obtained.

It was a further object of the invention to provide a novel diamine in order to control the profile of properties of applications in which diamines are used. In many applications, for example the use of the diamine as a hardener in epoxy resins, as an intermediate in the preparation of polyurethanes, as a starter in the preparation of polyetherols and as a monomer for polyamide preparation, a variation of different base units is required owing to the various demands and the different fields of use, in order to be able to adjust and influence, in a controlled manner, properties such as weathering stability, hydrolysis stability, chemical stability, light stability, and electrical and mechanical properties.

In addition, a process for preparing carvonediamine should be provided, in which only a low level of by-products which are difficult to remove from the reaction mixture is formed, for example the formation of dimers which can form in the course of reductive amination by coupling of two nitrile or keto groups of different molecules. More particularly, a high nitrile conversion and degree of saturation of the reaction product should be achieved, since nitrile amines or amino imines worsen the properties of the polymeric materials, and C—C double bonds can impair the colorfastness. Partly saturated compounds can generally, moreover, be removed from the saturated reaction product only with difficulty.

Furthermore, high process economy should be achieved by achieving high yields and selectivities.

Accordingly, the compound 5-isopropyl-3-aminomethyl-2-methyl-1-aminocyclohexane (carvonediamine) of the formula (I)

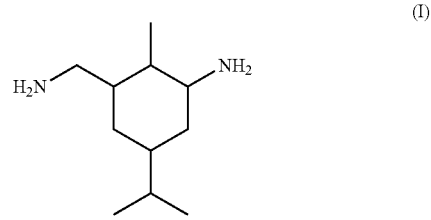

has been found.

The present invention further provides a process for preparing carvonediamine of the formula (I) by
a) reacting carvone of the formula (II)

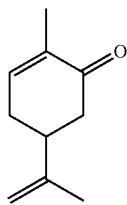

(II)

with hydrogen cyanide in the presence of a basic catalyst to give carvonenitrile of the formula (III)

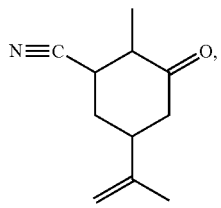

(III)

b) reacting the carvonenitrile obtained in stage a) with ammonia in the presence of an imine formation catalyst to give carvonenitrile imine of the formula (IV), and

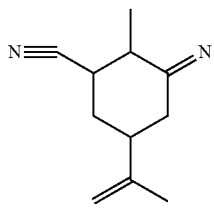

(IV)

c) reacting the carvonenitrile imine-containing reaction mixture obtained in stage b) with hydrogen and ammonia over hydrogenation catalysts.

In the process according to the invention for preparing carvonediamine, carvone is used as the starting material. Carvone is prepared and obtained as described, for example, in Ullmann's Encyclopedia of Industrial Chemistry, Verlag Chemie, Electronic Edition Release 2008, 7$^{th}$ Edition, chapter "Flavor and Fragrances". For example, carvone can be obtained by fractional distillation of caraway oil or peppermint oil, or by oxidation of limonene. Limonene in turn can be obtained by natural substance extraction. For example, limonene is obtained in large amounts as a by-product in orange juice production, or in the acid-catalyzed isomerization of α- and β-pinene.

Carvone can be used in the process in the form of the pure enantiomers (R-(−)-carvone or S-(+)-carvone), or as a racemic or enantiomerically enriched mixture.

R-(−)-Carvone is generally prepared from limonene from orange peel by oxidation with NOCl and elimination of HCl (R. H. Reitsema, Journal of Organic Chemistry, 1958, 2039). R-(−)-Carvone is also obtainable from spearmint. The S-(+)-carvone enantiomer occurs in caraway oil and dill oil. Like R-(−)-carvone, racemic carvone can be prepared from racemic limonene, which can be obtained from acid-catalyzed isomerization of pinene or Diels-Alder reaction of isoprene. Further methods are allylic oxidation with Pd(II) salts in the presence of Cu(II) and atmospheric oxygen (WO-A-99/12880) or uncatalyzed air oxidation of limonene. Typically, carvone is used in a purity of more than 90%, preferably more than 95% and more preferably more than 98%.

A further feedstock used in the process according to the invention is hydrogen cyanide (HCN). For the preparation of HCN, essentially the following processes are of significance: in the ammoxidation of methane (Andrussow process), a mixture of ammonia and methane is oxidized at about 1200° C. over a platinum mesh as a catalyst; in the ammodehydrogenation of methane (Degussa BMA process), ammonia and methane are converted with the aid of a catalyst to hydrogen cyamide and hydrogen, and, in the formamide splitting (BASF process), formamide is evaporated and heated strongly, which splits formamide into hydrogen cyamide and water.

The hydrocyanation of carvone is described, for example, in Chemistry & Industry (London, UK), 1967, (2), 1175.

In the process according to the invention for preparing carvonediamine, in a first stage a), carvone (5-isopropenyl-2-methylcyclohex-2-enone) is reacted with hydrogen cyanide (HCN) in the presence of a basic catalyst.

The reaction of carvone with hydrogen cyanide takes place in the presence of a basic catalyst. Suitable basic catalysts are all substances which form cyanide ions in the presence of hydrogen cyanide under the reaction conditions or comprise them. Examples include hydroxides, cyanides and alkoxides of the alkali metals and alkaline earth metals, and quaternary ammonium compounds. Preference is given to using alkali metal cyanides, alkali metal hydroxides, alkaline earth metal hydroxides and alkali metal $C_1$- to $C_4$-alkoxides such as sodium methoxide, sodium ethoxide, potassium methoxide, potassium tert-butoxide, lithium methoxide, particular preference to using sodium methoxide. Very particular preference is given to using NaCN, which can be prepared, for example, without isolation by contacting NaOH and HCN.

The catalyst concentration is between 0.01 and 3% by weight based on the reaction mixture. The catalyst concentration is preferably selected such that the solubility of the basic catalyst, which depends on the reaction temperature and the composition of the reaction mixture, is not exceeded; this is preferably a concentration between 0.01 and 0.3% by weight based on the reaction mixture.

The reaction of carvone with hydrogen cyanide can be performed at reaction temperatures of 80 to 220° C., preferably 100 to 180° C., more preferably 120 to 170° C.

The reaction pressure (measured absolute) is generally 0.05 to 2 MPa, preferably 0.09 to 1 MPa, more preferably atmospheric pressure (standard pressure) to 3 bar. The pressure can be generated, for example, by injecting inert gases (nitrogen).

In the inventive reaction of carvone with hydrogen cyanide, carvone is generally used in a molar excess based on the hydrogen cyanide, The molar carvone:HCN ratio of the two feedstocks, carvone and hydrogen cyanide (HCN), is typically 2:1 to 10:1, preferably 2:1 to 5:1, more preferably 2:1 to 3:1.

The reaction can be undertaken in the presence or absence of inert solvents. Suitable inert solvents for the reaction are water and $C_1$- to $C_{20}$-alkanols, preferably $C_1$- to $C_8$-alkanols, more preferably $C_1$- to $C_4$-alkanols, such as methanol, ethanol, n-propanol, isopropanol, n-butanol, isobutanol and tert-butanol, aliphatic hydrocarbons having 5 to 30 carbon atoms, preferably having 5 to 20 carbon atoms, more preferably having 5 to 10 carbon atoms, such as n-pentane, pentane isomer mixtures, n-hexane, hexane isomer mixtures, n-heptane, heptane isomer mixtures, n-octane, octane isomer mixtures, cycloaliphatic hydrocarbons having 5 to 20 carbon atoms, preferably having 5 to 12 carbon atoms, more preferably having 5 to 8 carbon atoms, such as cyclopentane, cyclohexane, cycloheptane and cyclooctane, amides such as dimethylformamide, dimethylacetamide, N-methylpyrrolidone, ureas such as N,N'-dimethylethyleneurea, N,N'-dimethylpropyleneurea, N,N,N',N'-tetra-n-butylurea, or carbonates such as ethylene carbonate and propylene carbonate.

Particular preference is given to using carvone in a molar excess, based on HCN, and to not adding any external solvent.

The inventive reaction of carvone with hydrogen cyanide can be performed batchwise, semicontinuously or preferably continuously.

Suitable reaction vessels and reactors are, for example, stirred reactors, tubular reactors, stirred vessel cascades, loop reactors or mixing circuits.

For example, a continuous process can be performed by feeding the basic catalyst, if appropriate dissolved in an inert solvent or in carvone, continuously into an apparatus in which carvone is reacted continuously with hydrogen cyanide under standard pressure or under elevated pressure (0.09 to 1 MPa, measured absolute).

Typically, the reaction is performed in a multistage stirred tank cascade.

However, it is also possible to perform the reaction in two separate reaction zones, the first reaction zone having essentially complete backmixing, and the second reaction zone having essentially no backmixing.

The reactor used for the first reaction zone with essentially complete backmixing may, for example, be a stirred tank, a mixing circuit or a loop reactor. The heat of reaction released is removed by means of suitable heat exchangers.

The suitable reactors for the second reaction zone which has essentially no backmixing are cylindrical reactors with random packings or fixed internals which completely or partially prevent backmixing. In the case of performance of the synthesis on the laboratory scale, however, it is also possible to use a tubular reactor which is operated in the turbulent flow range.

The residence time needed for full HCN conversion depends on the reaction temperature and the catalyst concentration. For the stirred reactor, it is generally 1 to 4 hours, and for the post reactor operated without backmixing generally 0.2 to 1.5 hours. A batchwise or semicontinuous process can be conducted by
a) initially charging carvone with the basic catalyst and adding hydrogen cyanide in an inert solvent or in carvone, or
b) initially charging carvone with hydrogen cyanide and adding the basic catalyst in an inert solvent or carvone, or
c) initially charging carvone and adding hydrogen cyanide and the basic catalyst in an inert solvent or carvone.

Variant a) is preferred here.

The reaction mixture obtained by reaction of carvone with hydrogen cyanide comprises carvone nitrile (5-isopropenyl-3-cyano-2-methylcyclohexanone) of the formula (III).

The resulting reaction mixture can be extracted with water in order to remove the dissolved catalyst.

However, the basic catalyst can also be neutralized by adding an equivalent or excess amount of an organic or inorganic acid.

To neutralize the reaction effluent, it is possible to use acids, for example inorganic acids such as phosphoric acid and sulfuric acid, or organic acids, for example sulfonic acids such as methanesulfonic acid, toluenesulfonic acid, carboxylic acids such as formic acid, acetic acid, propionic acid, malonic acid, 2-ethylhexanoic acid and adipic acid.

The reaction mixture can subsequently, if appropriate on completion of extraction with water or neutralization, be purified by fractional distillation.

This affords carvonenitrile (5-isopropenyl-3-cyano-2-methylcyclohexanone) of the formula (III).

Unconverted carvone can be recycled into the reaction process.

In stage b), the carvonenitrile obtained from stage a) is reacted with excess ammonia in the presence of an imine formation catalyst (imination).

Useful imine formation catalysts include, for example, solid Brønsted or Lewis acids, as described, for example, in EP-A1-449089 (page 2 column 2 lines 11-20), and in the article by Tanabe et al. (K. Tanabe, Studies in Surface Science and Catalysis, Vol. 51, 1989, p. 1 ff). Examples here include acidic metal oxide catalysts such as aluminum oxide, titanium dioxide, zirconium dioxide and silicon dioxide. Additionally useful are inorganic or organic ion exchangers laden with ammonium ions, such as zeolites or sulfonated copolymers of styrene and divinylbenzene (e.g. the Lewatit® brand from Lanxess, the Amberlite® brand from Rohm & Haas) or ion exchangers based on siloxane (for example the Deloxan® brand from Degussa).

Typically 5 to 500 mol of ammonia ($NH_3$), preferably 10 to 400 mol of $NH_3$, more preferably 20 to 300 mol of $NH_3$, are used per mole of carvonenitrile used.

Carvonenitrile can be iminated in the presence of a solvent, for example in alkanols or ethers, such as ethanol, butanol or tetrahydrofuran (THF). Preference is given to performing the imination of carvonenitrile without an addition of solvent.

The imination can be performed batchwise or preferably continuously.

The batchwise imination can be performed, for example, in a stirred autoclave, a bubble column or a circulation reactor, for instance a jet loop reactor.

In batchwise imination, a suspension of carvonenitrile and catalyst is typically initially charged in the reactor. In order to ensure a high conversion and high selectivity, the suspension of carvonenitrile and catalyst is typically mixed thoroughly with ammonia, for example by means of a turbine stirrer in an autoclave. The suspended catalyst material can be introduced and removed again with the aid of customary techniques (sedimentation, centrifugation, cake filtration, crossflow filtration). The catalyst can be used once or more than once.

The catalyst concentration is advantageously 0.1 to 50% by weight, preferably 0.5 to 40% by weight, more preferably 1 to 30% by weight, especially 5 to 20% by weight, based in each case on the total weight of the suspension consisting of carvonenitrile and catalyst.

The mean catalyst particle size is advantageously in the range from 0.001 to 1 mm, preferably in the range from 0.005 to 0.5 mm, especially 0.01 to 0.25 mm.

The imination is preferably performed continuously, typically in pressure vessels or pressure vessel cascades. Preference is given to passing carvonenitrile and $NH_3$ through a tubular reactor in which the imine formation catalyst is arranged in the form of a fixed bed.

In general, in the continuous imination, a catalyst hourly space velocity of 0.01 to 10 kg, preferably of 0.05 to 7 kg and more preferably of 0.1 to 5 kg of carvonenitrile per kg of catalyst and hour is established.

The imination is performed preferably within a temperature range from 20 to 150° C., preferably 30 to 130° C. and more preferably at 50 to 100° C.

The pressure in the imination is generally from 50 to 300 bar, preferably 100 to 250 bar.

The reaction mixture from imination typically comprises carvonenitrile imine and ammonia and unconverted carvonenitrile. The conversion of carvonenitrile to carvonenitrile imine is typically more than 80%, preferably more than 90% and more preferably more than 95%.

The reaction mixture from stage b) is reacted in stage c) with hydrogen and ammonia over hydrogenation catalysts (reductive amination).

The reaction mixture comprising carvonenitrile imine is converted preferably in liquid ammonia. Typically 5 to 500 mol of $NH_3$, preferably 10 to 400 mol of $NH_3$ and more preferably 20 to 300 mol of $NH_3$ are used per mole of carvonenitrile imine. Appropriately, in the preceding imination, the molar ratio between carvonenitrile and $NH_3$ is adjusted such that the molar ratio is also within a suitable range in the reductive amination. However, the $NH_3$ content can be increased to a desired value by adding additional $NH_3$ before the reductive amination.

A further starting material used for the reaction of the carvonenitrile imine-containing reaction mixture is hydrogen. The molar ratio between hydrogen and carvonenitrile imine is generally 3 to 10 000:1, preferably 4 to 5000:1 and more preferably 5 to 1000:1.

The hydrogen is supplied to the carvonenitrile imine-containing reaction mixture preferably after the imination and before the reductive amination. However, it is also conceivable that the hydrogen is supplied actually before the imination, since the imination is typically performed over catalysts which do not catalyze the hydrogenation. It is thus also possible for hydrogen supplied before the imination to be available as a starting material for the reaction of the carvonenitrile imine-containing reaction mixture during the reductive amination.

The hydrogenation catalysts used may in principle be all hydrogenation catalysts which comprise nickel, cobalt, iron, copper, ruthenium, palladium, platinum, rhodium and/or other metals of transition group VIII of the Periodic Table. Further suitable hydrogenation catalysts are catalysts which comprise the elements chromium, manganese, molybdenum, tungsten and/or rhenium.

Preference is given to using hydrogenation catalysts which comprise ruthenium, cobalt and/or nickel. Particular preference is given to catalysts which comprise ruthenium and/or cobalt.

The abovementioned hydrogenation catalysts can be doped in a customary manner with promoters, for example with chromium, iron, cobalt, manganese, thallium, molybdenum, titanium and/or phosphorus.

The catalytically active metals can be used as unsupported catalysts or on supports. Useful such supports include, for example, aluminum oxide, titanium dioxide, zirconium dioxide or magnesium oxide/aluminum oxide. The supports may also be imination-active in order to enable the reaction of ketone present in equilibrium with the imine during the hydrogenation of the imine group.

The hydrogenation catalysts useable in the process according to the invention are generally obtained by reducing so-called catalyst precursors with hydrogen.

The catalyst precursor typically comprises oxygen compounds of the abovementioned metals.

The catalyst precursors can be prepared by known processes, for example by precipitation, precipitative application or impregnation.

Such catalyst precursors are, for example, catalysts which are disclosed in EP-A-0636409 and whose catalytically active material, before the reduction with hydrogen, comprises 55 to 98% by weight of Co, calculated as CoO, 0.2 to 15% by weight of phosphorus, calculated as $H_3PO_4$, 0.2 to 15% by weight of manganese, calculated as $MnO_2$, and 0.2 to 15% by weight of alkali metal, calculated as $M_2O$ (M=alkali metal), or catalysts which are disclosed in EP-A-0742045 and whose catalytically active material, before the reduction with hydrogen, comprises 55 to 98% by weight of Co, calculated as CoO, 0.2 to 15% by weight of phosphorus, calculated as $H_3PO_4$, 0.2 to 15% by weight of manganese, calculated as $MnO_2$, and 0.05 to 5% by weight of alkali metal, calculated as $M_2O$ (M=alkali metal), or catalysts which are disclosed in EP-A-696572 and whose catalytically active material, before the reduction with hydrogen, comprises 20 to 85% by weight of $ZrO_2$, 1 to 30% by weight of oxygen compounds of copper, calculated as CuO, 30 to 70% by weight of oxygen compounds of nickel, calculated as NiO, 0.1 to 5% by weight of oxygen compounds of molybdenum, calculated as $MoO_3$, and 0 to 10% by weight of oxygen compounds of aluminum and/or of manganese, calculated as $Al_2O_3$ and $MnO_2$ respectively, for example the catalyst which is disclosed in loc. cit., page 8, and has the composition of 31.5% by weight of $ZrO_2$, 50% by weight of NiO, 17% by weight of CuO and 1.5% by weight of $MoO_3$.

The catalytically active metals can also be used in the form of sponge catalysts, known as Raney catalysts. The Raney catalysts used are preferably Raney cobalt catalysts, Raney nickel catalysts and/or Raney copper catalysts. Particular preference is given to using Raney cobalt catalysts.

The hydrogenation catalysts used may also advantageously be selective hydrogenation catalysts, selective hydrogenation catalysts being understood to mean those catalysts which preferentially hydrogenate the imine group over the nitrile group of the carvonenitrile imine.

Selective hydrogenation catalysts are, for example, hydrogenation catalysts which comprise ruthenium, palladium and/or rhodium. Preferred selective hydrogenation catalysts comprise ruthenium and/or rhodium, and particularly preferred selective hydrogenation catalysts comprise ruthenium.

The reductive amination is preferably performed in the presence of a basic compound and/or a basic hydrogenation catalyst.

This is understood to mean that the term "basic compound" does not include the ammonia reactant, but comprises one or more of the compounds listed below, or those compounds which act in a manner analogous to the compounds listed below. Suitable basic compounds include basic metal compounds, such as the oxides, hydroxides or carbonates of the alkali metals, alkaline earth metals or rare earth metals.

Preference is given to the metal compounds of the alkali metals and alkaline earth metals, such as the corresponding oxides, hydroxides and carbonates, such as $Li_2O$, $Na_2O$, $K_2O$, $Rb_2O$, $Cs_2O$, LiOH, NaOH, KOH, RbOH, CsOH, $Li_2CO_3$, $Na_2CO_3$, $K_2CO_3$, $Cs_2CO_3$, $Rb_2CO_3$, MgO, CaO, SrO, BaO, $Mg(OH)_2$, $Ca(OH)_2$, $Sr(OH)_2$, $Ba(OH)_2$, $MgCO_3$, $CaCO_3$, $SrCO_3$ or $BaCO_3$. Particular preference is given to LiOH, NaOH or KOH.

Preferred basic compounds which are likewise suitable are amines or ammonium hydroxides.

Particular preference is given to adding to the reaction mixture solutions of the basic compounds in water or other suitable solvents, such as alkanols, such as $C_1$-$C_4$-alkanols, e.g. methanol or ethanol, or ethers, such as cyclic ethers, e.g. THF or dioxane. Particular preference is given to adding solutions of alkali metal or alkaline earth metal hydroxides in water, particular preference to adding solutions of LiOH, NaOH or KOH in water.

Preferably, the concentration of the basic compound in water or other suitable solvents is 0.01 to 20% by weight, preferably 0.1 to 10 and more preferably 0.2 to 5% by weight.

The amount of the solution of the basic compound added is typically selected such that the ratio of the mass of the basic compound added to the mass of the carvonenitrile imine in the reaction mixture is 100 to 10 000:1 000 000, preferably 150 to 5000:1 000 000 and more preferably 200 to 1000:1 000 000.

The reductive amination can also be effected in the presence of basic hydrogenation catalysts. Such basic hydrogenation catalysts are abovementioned hydrogenation catalysts which have been doped with basic components, such as oxides or hydroxides of alkali metals, alkaline earth metals and rare earth metals, and/or applied to basic supports.

Suitable basic supports for hydrogenation catalysts are, for example, β-aluminum oxide or magnesium oxide/aluminum oxide mixtures, where the proportion of the magnesium oxide is preferably 5 to 40% by weight. The support comprising magnesium oxide and aluminum oxide may be amorphous or present in spinel form. Catalysts on basic supports are obtained industrially in a manner known per se. For example, ruthenium on basic support is obtained by applying aqueous ruthenium salt solutions, such as ruthenium chloride and ruthenium nitrate, to the appropriate basic support.

The concentration of the metals, especially ruthenium, on the basic supports is generally 0.1 to 10% by weight, preferably 0.5 to 5% by weight and more preferably 1 to 4% by weight.

Basic catalysts are also understood to mean those hydrogenation catalysts which are doped with the abovementioned basic components, such as oxides or hydroxides of alkali metals, alkaline earth metals and rare earth metals. Basic catalysts preferably comprise at least one basic component, such as $Li_2O$, $Na_2O$, $K_2O$, MgO, CaO, SrO or BaO.

The proportion of basic components, i.e. basic dopants, in basic hydrogenation catalysts, is generally more than 0.5% by weight and more preferably more than 0.7% by weight and more preferably more than 1% by weight, based on the total mass of the basic hydrogenation catalyst.

The hydrogenation catalysts described at the outset which have not been applied to basic supports as described above and/or which comprise 0.5% by weight or less of basic components, i.e. basic dopants, based on the total mass of the catalyst, are referred to hereinafter as nonbasic hydrogenation catalysts.

The reductive amination is effected typically at temperatures of 50 to 160° C. and a pressure of 50 to 300 bar.

The reductive amination can be performed batchwise or preferably continuously. The batchwise reductive amination can be performed, for example, in a stirred autoclave, a bubble column or a circulation reactor, for instance a jet loop reactor.

In batchwise reductive amination, a suspension of carvonenitrile imine and catalyst is typically initially charged in the reactor. In order to ensure a high conversion and high selectivity, the suspension of carvonenitrile imine and catalyst will typically be mixed thoroughly with hydrogen and the aminating agent, for example by means of a turbine stirrer in an autoclave. The suspended catalyst material can be introduced and removed again with the aid of customary techniques (sedimentation, centrifugation, cake filtration, cross-flow filtration). The catalyst can be used once or more than once.

The catalyst concentration is advantageously 0.1 to 50% by weight, preferably 0.5 to 40% by weight, more preferably 1 to 30% by weight, especially 5 to 20% by weight, based in each case on the total weight of the suspension consisting of carvonenitrile imine and catalyst.

The mean catalyst particle size is advantageously in the range from 0.001 to 1 mm, preferably in the range from 0.005 to 0.5 mm, especially 0.01 to 0.25 mm.

If appropriate, the reactants can be diluted with a suitable inert solvent in which 3-imino-5-isopropenyl-2-methylcyclohexanecarbonitrile has a good solubility, such as tetrahydrofuran, dioxane, N-methylpyrrolidone.

The continuous reductive amination can, for example, be performed in a continuous stirred autoclave, a continuous bubble column, a continuous circulation reactor, for instance a jet loop reactor, or a fixed bed reactor.

The continuous reductive amination is preferably performed in a tubular reactor with a fixed catalyst bed.

Especially suitable for this reaction is a tubular reactor with a fixed catalyst bed. The catalyst hourly space velocity in continuous mode is typically 0.01 to 10 kg, preferably from 0.05 to 7 kg and more preferably from 0.1 to 5 kg of carvonenitrile imine per kg of catalyst and hour.

Preference is given to effecting the reductive amination continuously in a tubular reactor with a fixed catalyst bed.

The reductive amination, i.e. the reaction of the carvonenitrile imine-containing reactant stream with hydrogen and ammonia over hydrogenation catalysts, can be effected in one reaction chamber or in a plurality of separate reaction chambers.

When the reductive amination is performed in only one reaction chamber, the temperature profile between reactor inlet and reactor outlet is typically very substantially constant and determined by the heat of reaction released in the reductive amination.

However, it is also possible to establish a temperature profile between reactor inlet and reactor outlet. The formation of such a temperature profile can be achieved by virtue of the temperature of individual regions of the reactor being controllable separately and individually. In such a case, it is advantageous when the temperature is increased between reactor inlet and reactor outlet. Preferably, the temperature at the reactor inlet is in the range from 50 to 100° C., while the temperature at the reactor outlet is between 100 and 160° C. The increasing temperature profile between reactor inlet and reactor outlet may be a constant function or increase in discrete steps.

In a preferred embodiment, the reductive amination, however, is effected in two or more stages, in which case the stages are effected in separate reaction chambers. In a particularly preferred embodiment, the reductive amination is performed in two stages, in which case the stages are effected in separate reaction chambers.

The first stage (stage I) is performed generally within a temperature range of 50 to 100° C., preferably at 55 to 95° C. and more preferably at 60 to 90° C., and at a pressure of 15 to 300, preferably 20 to 250 and more preferably 30 to 230 bar.

The second stage (stage II) is performed typically within a temperature range from 70 to 160° C., preferably 75 to 150° C. and more preferably at 80 to 140° C., and at a pressure of 50 to 300, preferably 80 to 250 and more preferably 100 to 230 bar. Both stages are typically each performed in pressure vessels, especially in fixed bed reactors.

The catalysts used in both stages may be the nonbasic and/or basic hydrogenation catalysts described at the outset, preference being given to using a nonbasic catalyst which comprises cobalt.

In further embodiments of the invention, it is possible to divide both stage I and stage II into further component stages, in which case the component stages are also each performed in separate reaction chambers.

For instance, it is possible to perform the component stages of stage I in two or more pressure vessels, especially fixed bed reactors.

As described above, the component stages of stage I are typically performed within a temperature range of 50 to 100° C. and at a pressure of 15 to 300 bar. Pressure and temperature in the component stages may be the same or different. Advantageously, the component stages are conducted at the same temperature and same pressure. When the component stages are conducted at different temperatures and pressures, it is advantageous when pressure and temperature increase from component stage to component stage, which means that the pressure and the temperature in the first component stage should be the lowest.

In each component stage, it is possible to use the nonbasic and/or basic hydrogenation catalysts described at the outset, preference being given to using nonbasic hydrogenation catalysts.

In a preferred embodiment, in the first component stage or in the first component stages of the first reaction stage, the nonbasic hydrogenation catalysts used are selective hydrogenation catalysts.

For reasons of process economy, it is advantageous when stage I of the reductive amination consists of not more than three and preferably two component stages, and more preferably one component stage, since the capital investment increases with increasing number of reactors.

When stage I of the reductive amination is performed in only one component stage, it is advantageous when the basicity of the reaction mixture in which the basic compound is contacted with the reaction mixture downstream of the outlet of stage I is increased.

In addition, it is possible to divide stage II of the reductive amination into further component stages, in which the component stages are preferably each performed in separate reaction chambers.

The component stages of stage II of the reductive amination are, as described above, typically performed within a temperature range from 70 to 160° C. and at a pressure from 50 to 300 bar. The component stages of stage II of the reductive amination are preferably performed in two or more pressure vessels, especially fixed bed reactors.

NH$_3$ and hydrogen are removed from the reaction effluent obtained from the reductive amination, if appropriate under pressure. The carvonediamine thus obtained can be isolated, for example, by a fractional rectification.

However, the reaction effluent obtained from the reductive amination can also be purified by crystallization or by chromatography.

The process according to the invention affords a mixture of stereoisomers of 5-isopropyl-3-aminomethyl-2-methyl-1-aminocyclohexane (carvonediamine). The isomer mixture formed may be racemic or enantiomerically enriched or enantiomerically pure. The stereoisomerism is partly determined in the stage of hydrocyanation, but is defined fully in the reductive amination/hydrogenation.

It is possible to regulate the stereoisomeric ratio in the reaction discharge by dividing the carvonenitrile imine-containing reactant stream before introduction into stage I of the reductive amination. One portion is passed together with hydrogen and NH$_3$ into stage I or into the first component stage of stage I, while the other portion is fed into a later stage (stage II) or component stage of stage I or stage II. A portion of the carvonenitrile imine-containing reactant stream is preferably fed into the second stage of the reductive amination (stage II) or into a component stage of the second stage of the reductive amination.

In general, the division of the reactant stream results in the thermodynamically preferred product being formed, such that the regulation of the division of the reactant stream allows the isomer ratio to be established. This is because, in the second hydrogenation stage, partial isomerization of the chiral centers can proceed, by virtue of the prochiral imino group or the keto group being formed again from the amino group. Through keto-enol tautomerism or imino-enamine tautomerism, it is then also possible for the adjacent methyl group to alter its spatial arrangement with respect to the ring plane.

A further means of controlling the stereoisomeric ratio consists in the regulation of the temperature in the first component stage of stage I. In both cases, the conversion of the reactant stream in the first component stage of stage I is ultimately regulated. The higher the conversion in stage I or the first component stage of stage I, typically, the higher the proportion of the kinetically preferred product in the product stream.

In a particularly preferred embodiment, the basicity of the reaction mixture is increased during the reaction of carvonenitrile imine with ammonia and hydrogen by contacting the reaction mixture with a basic compound other than ammonia and/or a basic catalyst once a portion of the carvonenitrile imine has been converted.

The basicity of the reaction mixture comprising carvonenitrile imine, ammonia, hydrogen and the hydrogenation catalyst can be increased by contacting the reaction mixture with a basic compound.

For instance, the basicity of the reaction mixture can be increased by adding a basic compound to the reaction mixture.

In a further embodiment, the basicity of the reaction mixture can be increased by contacting a basic hydrogenation catalyst with the reaction mixture.

In this particularly preferred embodiment, the basicity of the reaction mixture is increased during the reaction by contacting the reaction mixture with a basic compound once a portion of the carvonenitrile imine has been converted.

In general, the basicity is increased by contacting the reaction mixture with the basic compound once 1 to 95%, preferably 5 to 80% and more preferably 10 to 40% of the carvonenitrile imine in the reaction mixture has been converted.

Before increasing the basicity, generally no basic compounds are added to the reaction mixture. However, it is possible that the reaction mixture comprises small amounts of basic compounds. The ratio of the mass of the basic compound to the mass of the carvonenitrile imine in the reaction mixture before the increase in the basicity is preferably, however, less than 100:1 000 000, preferably less than 50:1 000 000.

Before the increase in the basicity, the reaction mixture is typically contacted with nonbasic catalysts.

When the reductive amination is performed in only one reaction chamber, for example in a fixed bed reactor, the increase in the basicity by the contacting of the reaction mixture with the basic compound can be effected in such a way that the metered addition of the basic compound is effected between the reactor inlet, into which the carvonenitrile imine-containing reactant stream is fed together with ammonia and hydrogen, and the reactor outlet. In this particularly preferred embodiment, the contacting of the reactant stream with the basic compound does not precede the reductive amination.

Since, as described above, the reaction is preferably effected under a high pressure, it is therefore generally necessary to undertake a metered addition of the basic compound at a high operating pressure in the reactor. Suitable industrial apparatus for metering in substances under high-pressure conditions are known to those skilled in the art. In particular, it is possible to use pumps such as high-pressure pumps or piston pumps to meter in substances under high-pressure conditions.

However, it is also possible that the basicity of the reaction mixture is increased by the contacting with a basic catalyst in such a way that the carvonenitrile imine-containing reactant stream is first passed with hydrogen and ammonia over one of the nonbasic hydrogenation catalysts described at the outset and then over a basic hydrogenation catalyst. This can be achieved by virtue of the catalysts being coated in a suitable manner.

Advantageously, at the transition between the layer of the nonbasic hydrogenation catalyst and that of the basic hydrogenation catalyst, as described above, a basic compound is metered in, since the basic components of the hydrogenation catalyst can be washed out with increasing operating time.

When the reductive amination, however, is performed in two stages, the stages typically being effected in separate reaction chambers, the increase in the basicity of the reaction mixture by contacting the reaction mixture with the basic compound can preferably be effected by metering in a solution of a basic compound between the outlet of stage I and the inlet of stage II.

However, the increase in the basicity of the reaction mixture by the contacting with a basic compound can also be effected in such a way that one of the nonbasic hydrogenation catalysts described at the outset is used in stage I and a basic hydrogenation catalyst is used in stage II.

Since the basic components can be washed out of the basic catalyst with increasing operating time, it is advantageous when a solution of a basic compound is additionally metered in between the outlet of stage I and the inlet of stage II.

In a particularly preferred embodiment, the nonbasic hydrogenation catalysts used in stage I are the selective hydrogenation catalysts described at the outset.

When stage I of the reductive amination is performed in two or more component stages, it is advisable to increase the basicity of the reaction mixture by undertaking the contacting of the reaction mixture with the basic compound after the first component stage of stage I.

Preference is given to contacting the reaction mixture with the basic compound by metering in the basic compound between the outlet of one component stage and the inlet of the next component stage of stage I.

Advantageously, the basic compound is metered in between the first component stage and the second component stage of stage I. However, it is also possible to meter in the basic compound between the outlet and the inlet of any two successive component stages. The basic compound is generally not metered in upstream of the first component stage of stage I.

The increase in the basicity of the reaction mixture by the contacting with a basic hydrogenation catalyst can also be effected in such a way that one of the nonbasic hydrogenation catalysts described at the outset is used in the first component stage or in the first component stages, and a basic hydrogenation catalyst is used in one of the downstream component stages. It is also conceivable that a layer arrangement of nonbasic hydrogenation catalysts and basic hydrogenation catalysts is effected in the component stages.

Furthermore, it is advantageous to additionally undertake the metered addition of a solution of a basic compound into the component stages with basic hydrogenation catalysts, in order to compensate for the possibility of the basic components being washed out of the basic hydrogenation catalyst.

The increase in the basicity of the reaction mixture by the contacting of the reaction mixture with a basic compound and/or a basic hydrogenation catalyst should preferably precede stage II. However, it is also possible to undertake the contacting of the reaction mixture in one of the component stages of the second reaction stage. This can be done in an analogous manner by metering in a solution of a basic compound between the component stages of stage II, or using a basic hydrogenation catalyst after the first component stage of stage II.

In addition, a layer arrangement of hydrogenation catalysts and basic hydrogenation catalysts in the component stages of stage II is possible.

The present invention additionally relates to the use of 5-isopropyl-3-aminomethyl-2-methyl-1-aminocyclohexane (carvonediamine) as a hardener for epoxy resins, as an intermediate in the preparation of diisocyanates, as a starter in the preparation of polyetherols and/or as a monomer for polyamide preparation.

5-Isopropyl-3-aminomethyl-2-methyl-1-aminocyclohexane (carvonediamine) constitutes an alternative hardener for epoxy resins, which enables new possibilities in the formulation and processing of epoxy resins and can be used to regulate the spectrum of properties of epoxy resins. Similarly to IPDA, carvonediamine has both an amine group bonded directly to the ring and an amino group joined to the aliphatic ring via a methylene group. Carvonediamine thus exhibits similar reactivity behavior to IPDA and can in many cases be used as a substitute for IPDA.

5-Isopropyl-3-aminomethyl-2-methyl-1-aminocyclohexane (carvonediamine) can also be used as an intermediate in the preparation of carvone diisocyanate (5-isopropyl-3-isocyanatomethyl-2-methyl-1-isocyanatocyclohexane) of the formula (V).

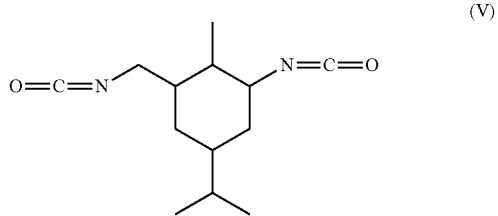 [SMILES: CC(C)C1CC(CN=C=O)C(C)C(N=C=O)C1]

(V)

This diisocyanate is suitable for the preparation of light-stable polyurethanes, for example as a varnish or coating, and, owing to its structure, offers new formulation possibilities and hence access to novel, interesting profiles of properties. Carvone diisocyanate is obtainable, for example, by reaction of carvonediamine with phosgene.

5-Isopropyl-3-aminomethyl-2-methyl-1-aminocyclohexane (carvonediamine) can also be used as a starter in the preparation of polyetherols. 5-Isopropyl-3-aminomethyl-2-methyl-1-aminocyclohexane (carvonediamine) is a CH-acidic compound which can be deprotonated with a base and onto which alkylene oxides, such as ethylene oxide, propylene oxide and/or butylene oxide, can subsequently be added. Alkoxylated diamines can be used, for example, as catalysts in PU production.

In addition, 5-isopropyl-3-aminomethyl-2-methyl-1-aminocyclohexane (carvonediamine) can be used as a monomer in the preparation of polyamides. For instance, 5-isopropyl-3-aminomethyl-2-methyl-1-aminocyclohexane (carvonediamine) can be reacted, for example, with dicarboxylic acids, for example succinic acid, adipic acid, terephthalic acid and/or phthalic acid, to give polymers.

By means of the invention described, it is possible to achieve a high carvonediamine yield. The stereoisomeric ratio can be regulated by adjusting the reaction conditions. The process described can be operated with a high space-time yield. The formation of troublesome by-products, more particularly dimers, is very substantially avoided. A particular feature of the process is the achievement of a maximum nitrile conversion and degree of saturation of the reaction product, since, for optimal properties in polymers, no nitrile amines, amino imines and olefin residues may be present. Partly saturated compounds can generally be removed from saturated compounds only with difficulty.

Carvonediamine can be utilized in the preparation of polymer materials, such as epoxy resins, polyurethanes, polyesters, etc., in order to regulate the profile of properties of these polymer materials, for example with regard to weathering stability, hydrolysis stability, chemical stability, light stability, and electrical and mechanical properties, and thus allows greater possible variation in the formulation of these materials.

By means of the present invention, it was possible to obtain a diamine which, similarly to IPDA, has both an amine group bonded directly to the ring and an amino group joined to the aliphatic ring via a methylene group. Carvonediamine should therefore have a similar reactivity profile to IPDA, and be usable as a substitute for IPDA in many applications.

Carvonediamine can additionally be produced on the basis of renewable raw materials. The use of carvonediamine instead of feedstocks produced on a petrochemical basis can thus protect natural gas and oil reserves. The renewable carvone raw material is typically not used as a food or as a raw material for the foods industry, and so its use should not contribute to a shortage of food.

The invention is illustrated in the examples which follow.

EXAMPLES

Example 1

Conversion of Carvone to Carvonenitrile 1379.4 g (9 mol) of R-(−)-carvone (5-isoprenyl-2-methylcyclohex-2-enone) with a purity of 98% (5-isoprenyl-2-methylcyclohex-2-enone) were heated in a 4000 ml glass flask to approx. 150° C. with stirring. At 144° C., 18.4 g of 30% sodium methoxide in water (0.1 mol) were added and then a mixture of 1287.9 g (8.4 mol) of 98% R-(−)-carvone (5-isoprenyl-2-methylcyclohex-2-enone) and 330.5 g (12.15 mol) of hydrogen cyamide (HCN) was added dropwise at 136-148° C. with stirring within 8 h. The postreaction time was approx. one hour. Subsequently, the HCN conversion was checked, and was 99.5%. The entire raw output weighed 3014 g and had a dark red color. The raw output was distilled through a Vigreux column. The first fraction recovered was unconverted carvone (approx. 900 g), and, after a mixed fraction (147.5 g), 1809.8 g of carvonenitrile were obtained with a purity of 98-99% (gas chromatography).

The yield including the product of value present in the mixed fraction was 93.7% based on HCN.

Example 2

Conversion of Carvonenitrile to Carvonediamine

The apparatus used consisted of 8 tubular reactors connected in series (2 tubes with dimensions of 1500×6×1 mm (C1-C2) and 6 tubes with dimensions of in each case 2000× 8×1.5 mm (C3-C8)). The first two reactors C1-C2 were filled with 15.7 g of $TiO_2$ extrudates with an extrudate diameter of 1.5 mm; the remaining 6 reactors were each filled with approx. 85 g of a hydrogenation catalyst ($Mn_3O_4$ 5-6.2%, $Na_2O$ 0-0.5%, $H_3PO_4$ 2.8-3.8%, remainder Co+CoO), which had been reduced with hydrogen at 280° C. at a pressure of 1 bar for 24 hours.

By means of jacket heating with oil, the temperature was adjusted to 60° C. in reactors C1 and C2, to 90° C. in reactors C3-C4, to 115° C. in reactors C5-C6, and to 130° C. in reactors C7-C8. Between reactors C2 and C3, hydrogen was fed under pressure (230 bar) into the reaction mixture.

23 g per hour of a mixture of THF and carvonenitrile in a ratio of 1:1 together with 73 g per hour of $NH_3$ were pumped into the first reactor (C1), and another 17 standard liters/h of hydrogen were fed in upstream of reactor C3. The reaction discharge was decompressed through a regulating valve. In a downstream phase separator, hydrogen was subsequently removed and ammonia was evaporated off.

After an operating time of 21.5 hours, a sample of the reaction discharge was analyzed by means of gas chromatography. The reaction discharge had the following composition (the contents of the compounds by means of gas chromatography were determined as area percentages. The area percentages of the signals are based here on the total area below the signals measured with the exception of the water signal and of the ammonia signal.):

3.86% of a bicyclic amine of the general formula VI, 0.68% of an isomeric bicyclic amine of the formula VI,

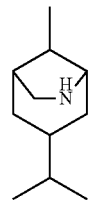

(VI)

and a total of 89.16% of carvonediamine as a mixture of 4 diastereoisomers.

In addition, 1.5% of incompletely hydrogenated compounds were present, which possessed either unsaturated CN or CC bonds.

The crude product which was obtained within an operating time of 45 hours and collected was freed of THF and purified by distillation.

At an operating pressure of 10 mbar, the carvonediamine product of value distilled over at 129-130° C.

From 1024 g of low-THF crude product, 791 g of carvonediamine were obtained as an isomer mixture with a carvonediamine content of more than 99% (GC analysis), which corresponds to a yield of 74% based on 1035 g of carvonenitrile used.

The isomer mixture of carvonediamine was characterized by GC-MS, NMR and elemental analysis.

In the GC-MS according to the method of 30 m db1701, 1 micrometer, start temperature 80° C., temperature ramp 10° C./min to 280° C., 4 main peaks which correspond to the corresponding pure diastereoisomers of carvonediamine were detected: retention time 17.41 min. (12.4 area %), 17.45 min. (11.4 area %), 17.72 min. (17.1 area %) and 18.23 min. (58.5 area %). The purity was thus 99.4% by GC.

$^1$H NMR (500 MHz, DMSO): 0.6-0.8 (part of a dedoubled doublet, 1.5H), 0.8-0.95 (signal cluster, 8.5H), 1.0-1.5 (signal cluster, 8H), 1.55-1.92 (signal cluster, 3H), 2.25-2.85 (m, 3H).

The following fragment distributions were obtained (M+=184, corresponds in each case to the molecular peak):

Peak No. 1:
m/z (%)=18 (5), 27 (8), 28 (10), 29 (10), 30 (93), 39 (10), 41 (33), 42 (14), 43 (41), 44 (16), 45 (3), 53 (9), 54 (6), 55 (46), 56 (81), 57 (54), 58 (7), 65 (3), 67 (15), 68 (12), 69 (27), 70 (30), 71 (19), 72 (5), 77 (6), 79 (14), 80 (6), 81 (29), 82 (41), 83 (13), 84 (35), 85 (4), 91 (6), 93 (8), 94 (9), 95 (46), 96 (16), 97(6), 98 (28), 99 (3), 106 (3), 107 (17), 108 (5), 109 (8), 110 (8), 111 (4), 112 (15), 121 (3), 122 (3), 123 (4), 124 (100), 125 (15), 126 (3), 135 (4), 136 (6), 137 (4), 138 (19), 139 (3), 141 (29), 142 (4), 150 (10), 152 (8), 154 (19), 155 (14), 184 (5)

Peak No. 2:
m/z (%)=18 (4), 27 (6), 28(5), 29 (8), 30 (70), 39 (7), 41 (25), 42 (10), 43 (31), 44 (12), 45 (4), 53 (7), 54 (5), 55 (38), 56 (38), 57 (31), 58 (6), 65 (3), 67 (10), 68 (8), 69 (21), 70 (24), 71 (16), 72 (5), 77 (5), 79 (11), 80 (3), 81 (21), 82 (28), 83 (10), 84 (35), 85 (5), 91 (5), 93 (6), 94 (6), 95 (29), 96 (10), 97 (5), 96 (30), 99 (3), 101 (3), 107 (11), 108 (4), 109 (6), 110 (8), 111 (4), 112 (14), 123 (3), 124 (100), 125 (21), 126 (4), 137 (3), 138 (14), 141 (30), 142 (6), 150 (3), 152 (6), 154 (26), 155 (9), 184 (3)

Peak No. 3:
m/z (%)=18 (3), 27 (5), 28 (8), 29 (6), 30 (54), 39 (6), 41 (22), 42 (10), 43 (28), 44 (9), 53 (6), 54 (4), 55 (25), 56 (36), 57 (16), 58 (4), 67 (10), 68 (8), 69 (16), 70 (25), 71 (70), 72 (7), 77 (4), 79 (9), 80 (84), 81 (16), 82 (32), 83 (9), 84 (21), 91 (4), 93 (5), 94 (5), 95 (28), 96 (13), 97 (3), 98 (15), 107 (9), 108 (3), 109 (5), 110 (12), 111 (3), 112 (8), 138 (8), 141 (11), 152 (6), 154 (11), 155 (6)

Peak No. 4:
m/z (%)=18 (4), 27 (7), 28 (11), 29 (8), 30 (68), 39 (8), 41 (29), 42 (12), 43 (36), 44 (13), 45 (3), 53 (8), 54 (5), 55 (33), 56 (100), 57 (51), 58 (6), 67 (13), 68 (11), 69 (21), 70 (32), 71 (27), 72 (5), 77 (5), 79 (12), 80 (5), 81 (23), 82 (42), 83 (12), 84 (28), 85 (3), 91 (6), 93 (7), 94 (8), 95 (37), 96 (16), 97 (5), 98 (20), 107(14), 108 (4), 109 (7), 111 (4), 112 (17), 121 (3), 123 (4), 124 (84), 125 (21), 126 (4), 135 (4), 136 (5), 137 (3), 138 (15), 141 (22), 142 (3), 150 (5), 152 (10), 154 (30), 155 (17), 169 (3), 184 (4)

To determine the elemental analyses, a Vario El III automatic analyzer from Elementar was used.

The elemental analysis gave:
C=71.3 (expected: 71.7); N=15.6 (expected: 15.2); H=13.4 (expected: 13.1) g/100 g Example 3

Comparison of the Hardening of DGEBA (Diglycidyl Ether of Bisphenol A) with Isophoronediamine (IPDA) and Carvonediamine The formulations used had the following composition:
Formulation 1: 17.96 g of DGEBA, 4.10 g of IPDA
Formulation 2: 29.51 g of DGEBA, 7.27 g of carvonediamine Before the hardening, the components of the formulation were mixed at 3000 rpm (Speedmixer DAC 150 FVZ) for two minutes.

After the mixing, approx. 15.5 g of the particular formulation were poured into aluminum dishes of dimensions 7×3.5×3 cm (L×W×H), in order to produce resin slabs with a layer thickness of 3-4 mm. The resin slabs were hardened at 60° C., 80° C., 100° C., 120° C., 140° C., 160° C. and 180° C. for 30 min each.

In parallel to the production of the slabs, the hardening of the particular formulation was studied by means of DSC. To this end, typically 3 to 10 mg of resin formulation were used. The measurements were effected under air on a DSC822$^e$ unit from Mettler Toledo in dynamic mode with a heating rate of 10° C./min. Onset temperatures $T_o$ (tangent onset of the exothermicity peaks), peak maxima $T_{max}$ and reaction enthalpies ΔH of the polymerization reactions are summarized in Table 1.

To determine the glass transition temperatures, samples, typically a few mg, were taken from the hardened resin slabs and these were used to determine the glass transition temperatures $T_g$ by means of DSC (3 heating segments with a heating rate of 30° C./min, determination from the mean of segments 2 and 3).

In addition, a thermogravimetric analysis (TGA) in a nitrogen stream was used to study the decomposition of the polymer and to determine the time of 5% mass loss (5% degradation). The measurements were performed with a TGA/SDTA851$^e$ instrument from Mettler Toledo.

The pot life at 100° C. was determined with the aid of a GELNORM®-RVN pot life measuring instrument, by recording the relative viscosities at this temperature. The data provide an important indication of the duration of hardening.

The products were studied by DSC and TGA.

TABLE 1

Hardening of DGEBA (9) with isophoronediamine (1) or carvonediamine

| Formulation | Amount of resin [g] | Amount of hardener [g] | $T_O$ [° C.] | $T_{max}$ [° C.] | ΔH [J/g] | $T_g$ [° C.] | Appearance of slabs | TGA 5% degradation [° C.] | Pot life at 100° C. [sec] |
|---|---|---|---|---|---|---|---|---|---|
| 1 | 17.96 | 4.10 | 59 | 108 | 426 | 160 | Clear, transparent, firm | 355 | 490-620 |
| 2 | 29.51 | 7.27 | 82 | 118 | 390 | 159 | Clear, transparent, firm | 355 | 540-580 |

The invention claimed is:

1. 5-Isopropyl-3-aminomethyl-2-methyl-1-aminocyclohexane (carvonediamine) of the formula (I)

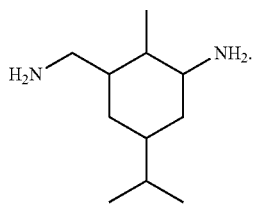

(I)

2. A process for preparing carvonediamine of the formula (I)

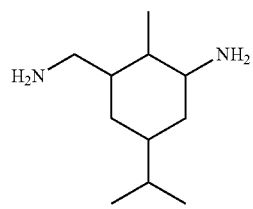

(I)

by
a) reacting carvone of the formula (II)

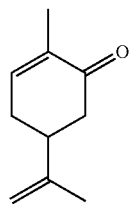

(II)

with hydrogen cyanide in the presence of a basic catalyst to give carvonenitrile of the formula (III)

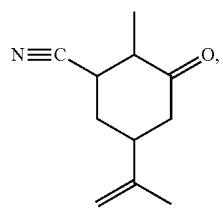

(III)

b) reacting the carvonenitrile obtained in stage a) with ammonia in the presence of an imine formation catalyst to give carvonenitrile imine of the formula (IV), and

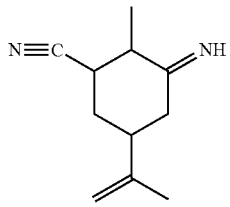

(IV)

c) reacting the carvonenitrile imine-containing reaction mixture obtained in stage b) with hydrogen and ammonia over hydrogenation catalysts.

3. The process according to claim 2, wherein the basic catalyst used in stage a) is sodium hydroxide, sodium cyanide or sodium methoxide.

4. The process according to claim 2, wherein the imine formation catalyst used comprises one or more acidic metal oxide catalysts such as aluminum oxide, titanium dioxide, zirconium dioxide and silicon dioxide.

5. The process according to claim 2, wherein stage c) is performed in the presence of a basic compound other than ammonia and/or a basic catalyst.

6. The process according to claim 2, wherein the basicity of the reaction mixture is increased in stage c) during the reaction by contacting the reaction mixture with a basic compound other than ammonia and/or a basic catalyst once a portion of the carvonenitrile imine has been converted.

7. The process according to claim 6, wherein the increase in basicity is preceded by use of a nonbasic hydrogenation catalyst.

8. The process according to claim 6, wherein the basicity of the reaction mixture is increased by adding a basic compound as a solution and selecting the amount of the basic compound added as a solution such that the ratio of the mass of the basic compound added to the mass of the carvonenitrile imine in the reactant stream is 100 to 10 000:1 000 000.

9. The process according to claim 6, wherein the basicity of the reaction mixture is increased by using, as basic compounds, a basic hydrogenation catalyst, where the proportion of basic components in the basic hydrogenation catalyst is at least 0.5% by weight based on the total mass of the basic hydrogenation catalyst and/or the hydrogenation catalyst is supported on a basic support.

10. The process according to claim 2, wherein a cobalt-containing hydrogenation catalyst is used.

11. The process according to claim 2, wherein the reaction in stage c) is performed in two stages (stage I and stage II).

12. The process according to claim 11, wherein stage I is performed within a temperature range of 50 to 100° C. at a pressure of 15 to 300 bar, and stage II within a temperature range of 70 to 160° C. at a pressure of 50 to 300 bar.

13. The process according to claim 12, wherein a ruthenium- and/or rhodium-containing catalyst is used in stage I.

14. The process according to claim 11, wherein the reaction mixture is contacted with the basic compound after stage I.

15. The process according to claim 11, wherein stage I and/or stage II is performed in two or more component stages, the reaction mixture being contacted with the basic compound no earlier than after the first component stage of stage I.

16. The process according to claim 11, wherein the reactant stream is divided by passing a portion of the reactant stream into stage I and a portion of the reactant stream directly into stage II.

17. The process according to claim 2, wherein the basicity is increased once 5 to 80% of carvonenitrile imine has been converted.

18. The process according to claim 2, wherein the carvone of the formula (II) is based on renewable raw materials.

19. A hardener for epoxy resins, an intermediate in the preparation of diisocyanates, a starter in the preparation of polyetherols or a monomer for polyamide preparation comprising the carvonediamine of claim 1.

* * * * *